United States Patent
Winstrom

(10) Patent No.: US 8,332,040 B1
(45) Date of Patent: Dec. 11, 2012

(54) EXTERNAL CHARGING DEVICE FOR CHARGING AN IMPLANTABLE MEDICAL DEVICE AND METHODS OF REGULATING DUTY OF CYCLE OF AN EXTERNAL CHARGING DEVICE

(75) Inventor: William L. Winstrom, Austin, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 879 days.

(21) Appl. No.: 12/401,377

(22) Filed: Mar. 10, 2009

Related U.S. Application Data

(60) Provisional application No. 61/035,131, filed on Mar. 10, 2008.

(51) Int. Cl.
*A61N 1/08* (2006.01)
(52) U.S. Cl. ......................................................... 607/61
(58) Field of Classification Search ............... 607/30–32, 607/59–61, 33
See application file for complete search history.

(56) References Cited

U.S. PATENT DOCUMENTS

| | | | |
|---|---|---|---|
| 5,411,537 A | 5/1995 | Munshi et al. | |
| 5,702,431 A * | 12/1997 | Wang et al. | 607/61 |
| 6,067,474 A * | 5/2000 | Schulman et al. | 607/57 |
| 6,278,258 B1 | 8/2001 | Echarri et al. | |
| 6,772,011 B2 * | 8/2004 | Dolgin | 607/61 |
| 7,155,291 B2 | 12/2006 | Zarinetchi et al. | |
| 2002/0055763 A1 | 5/2002 | Zarinetchi et al. | |
| 2005/0288739 A1 | 12/2005 | Hassler, Jr. et al. | |
| 2006/0020307 A1 | 1/2006 | Davis et al. | |
| 2009/0157145 A1 | 6/2009 | Cauller | |

\* cited by examiner

*Primary Examiner* — Scott Getzow
*Assistant Examiner* — Amanda Patton
(74) *Attorney, Agent, or Firm* — Christopher S. L. Crawford; Craig Hoersten

(57) ABSTRACT

In one embodiment, an external charging device for recharging an implanted medical device, comprises: a battery for powering the external charging device; a coil for radiating RF power; drive circuitry for driving the coil according to a duty cycle; circuitry for generating a signal that is indicative of an amount of current flowing through the coil; and control circuitry for controlling the drive circuitry, wherein the control circuitry is operable to process the signal from the circuitry for generating to detect when a coil of the implantable medical device temporarily ceases absorbing RF power, the control circuitry modifying the duty cycle in response to detection of the coil of the implantable medical device temporarily ceasing absorbing RF power.

14 Claims, 5 Drawing Sheets

US 8,332,040 B1

EXTERNAL CHARGING DEVICE FOR CHARGING AN IMPLANTABLE MEDICAL DEVICE AND METHODS OF REGULATING DUTY OF CYCLE OF AN EXTERNAL CHARGING DEVICE

CROSS-REFERENCE TO RELATED APPLICATIONS

This application claims the benefit of U.S. Provisional Application No. 61/035,131, filed Mar. 10, 2008, which is incorporated herein by reference.

TECHNICAL FIELD

The present application is generally related to systems and methods for regulating a duty cycle for an external charging device that is charging an implantable medical device.

BACKGROUND

Neurostimulation systems are devices that generate electrical pulses and deliver the pulses to nerve tissue to treat a variety of disorders. Spinal cord stimulation (SCS) is an example of neurostimulation in which electrical pulses are delivered to nerve tissue in the spine for the purpose of chronic pain control. Other examples include deep brain stimulation, cortical stimulation, cochlear nerve stimulation, peripheral nerve stimulation, vagal nerve stimulation, sacral nerve stimulation, etc. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

Neurostimulation systems generally include a pulse generator and one or more leads. The pulse generator is typically implemented using a metallic housing that encloses circuitry for generating the electrical pulses, control circuitry, communication circuitry, a rechargeable battery, recharging circuitry, etc. The pulse generation circuitry is coupled to one or more stimulation leads through electrical connections provided in a "header" of the pulse generator. Stimulation leads typically include multiple wire conductors enclosed or embedded within a lead body of insulative material. Terminals and electrodes are located on the proximal and distal ends of the leads. The conductors of the leads electrically couple the terminals to the electrodes. The electrical pulses from the pulse generator are conducted through the leads and applied to patient tissue by the electrodes of the leads.

Recharging of an implanted pulse generator typically occurs by near-field coupling of a coil in the implanted pulse generator with a coil of an external charging device (which could also function as a programming device). The external charging device radiates power from its coil which induces current in the coil of the implanted pulse generator. The recharging circuitry of the implanted pulse generator rectifies the induced current and charges the battery of the implanted pulse generator (subject to various regulation circuitry).

SUMMARY

In one embodiment, an external charging device for recharging an implantable medical device, comprises: a battery for powering the external charging device; a coil for radiating RF power; drive circuitry for driving the coil according to a duty cycle; circuitry for generating a signal that is indicative of an amount of current flowing through the coil; and control circuitry for controlling the drive circuitry, wherein the control circuitry is operable to process the signal from the circuitry for generating to detect when a coil of the implantable medical device temporarily ceases absorbing RF power, the control circuitry modifying the duty cycle in response to detection of the coil of the implantable medical device temporarily ceasing absorbing RF power.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

Figure 1:
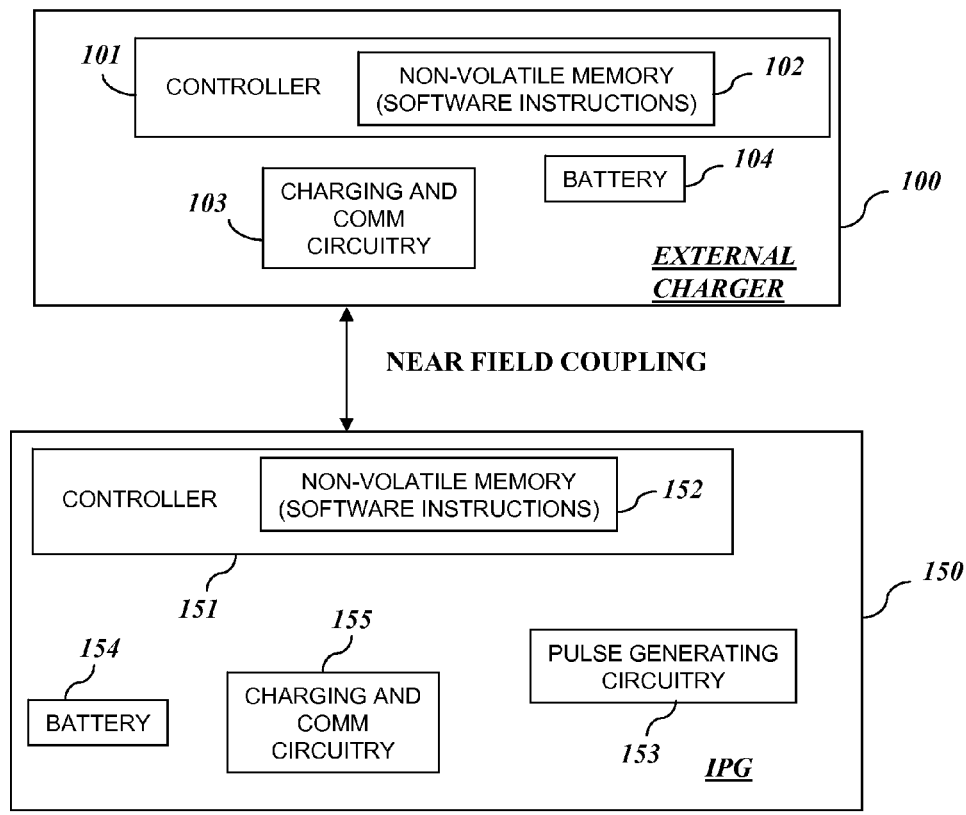
FIG. 1 depicts block diagrams of an external charging device and an implantable pulse generator according to one representative embodiment.

FIG. 1 depicts block diagrams of external charger 100 and implantable pulse generator (IPG) 150 according to one representative embodiment. Charger 100 comprises controller 101 (e.g., any suitable commercially available microcontroller) for controlling the operations of charger 100 according to instructions stored in non-volatile memory 102. Charger 100 is powered by battery 104. In preferred embodiments, battery 104 is a rechargeable lithium ion battery. External charger 100 further comprises charging and communication circuitry 103. Charging and communication circuitry 103 may be adapted, in some embodiments, to electrically couple to a coil of an external wand (shown in FIG. 4) that is held, during charging, by the patient about the patient's body immediately adjacent to the implant site of IPG 150. Alternatively, the coil may be integrated in the same device package with the circuitry of charger 100. Charging and communication circuitry 103 drives the coil using a suitable RF signal for charging purposes. Charging and communication circuitry 103 also drives the coil using a suitable modulated RF signal to communicate data to IPG 150. Charger 100 may also be adapted for use as a controller to control the operations of IPG 150 by communicating suitable control parameters using circuitry 103.

IPG 150 comprises controller 151 (e.g., any suitable commercially available microcontroller) for controlling the pulse generating and other operations of IPG 150 according to instructions stored in non-volatile memory 152. IPG 150 comprises pulse generating circuitry 153 for generating stimulation pulses for delivery to tissue of the patient. Any suitable existing or later developed pulse generating circuitry may be employed. An example of pulse generating circuitry is described in U.S. Patent Application Publication No. 2006/0259098, entitled "SYSTEMS AND METHODS FOR USE IN PULSE GENERATION," which is incorporated herein by reference. Pulse generating circuitry 153 may comprise one or multiple pulse sources. Also, pulse generating circuitry 153 may operate according to constant voltage stimulation, constant current stimulation, or any other suitable mode of operation. IPG 150 may be adapted for spinal cord stimulation, peripheral nerve stimulation, peripheral nerve field stimulation, deep brain stimulation, cortical stimulation, gastric pacing, cardiac therapies, and/or the like. Although an IPG is discussed in regard to one embodiment, representative embodiments may be employed to recharge any type of implantable medical device.

The various components of IPG 150 are powered by battery 154 (preferably a lithium ion rechargeable battery). Battery 154 is recharged by converting RF power radiated from external charger 100. Charging and communication circuitry 155 preferably comprises a coil (shown in FIG. 3) for near-field coupling with the coil of external charger 100. When external charger 100 radiates RF power using its coil, the inductive coupling between the coil of charger 100 with the coil of IPG 150 causes current to be induced in the coil of IPG 150. Circuitry 155 uses the induced current to charge battery 154. Also, circuitry 155 preferably uses the same coil to communicate with charger 100.

Figure 2:
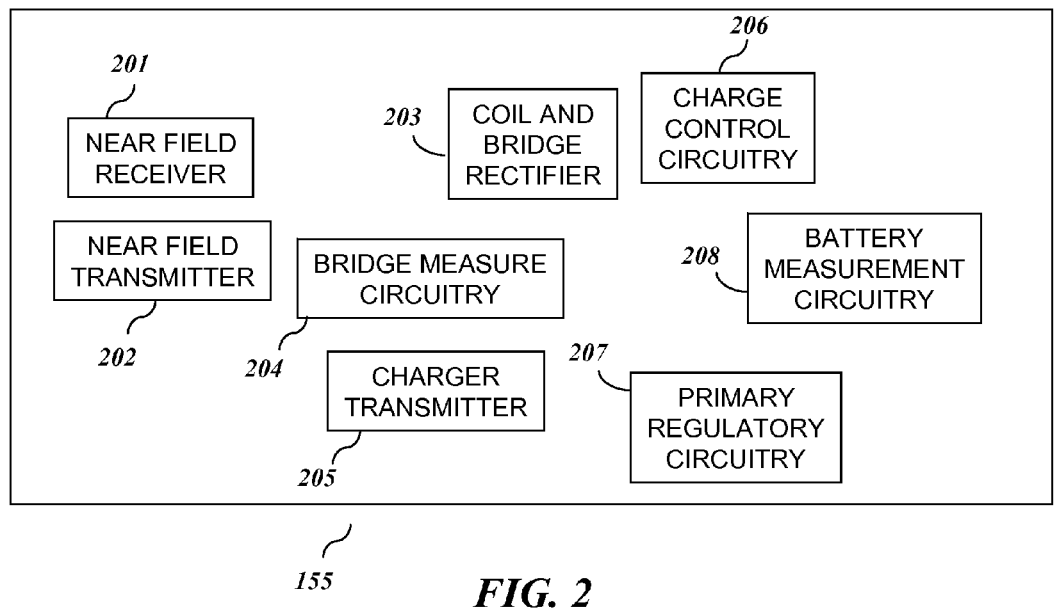
FIG. 2 depicts a block diagram of charge control and communication circuitry of an implantable pulse generator according to one representative embodiment.

FIG. 2 depicts a block diagram of circuitry 155 according to one representative embodiment. Circuitry 155 comprises coil and bridge rectifier circuitry 203. The coil of circuitry 203 is used both for charging operations and for communication with charger 100. Near field receiver 201 is coupled to the coil (through capacitor 302 shown in FIG. 3) to the coil. Receiver 201 demodulates data when a carrier at an appropriate frequency is detected. Receiver 201 communicates a serial data stream to controller 151. Near field transmitter 202 receives a serial data stream from controller 151 and generates a modulated RF signal for application to coil 301 to communicate data to charger 100. Signal modulation and demodulation may, alternatively, be implemented in software executing on controller 151. In preferred embodiments, near field receiver 201 and transmitter 202 do not operate when charging operations are taking place. Accordingly, charger transmitter 205 is employed to provide charging status messages to charger 100 when charging is occurring.

Bridge measure circuitry 204 measures the output voltage (the voltage on VCHG 309 in FIG. 3) of circuitry 155 for control of charging operations. Primary regulatory circuitry 207 preferably operates to control charging operations in response to the measurement signal from circuitry 204. When the output voltage is relatively low, regulatory circuitry 207 permits circuitry 155 to absorb RF power. When the output voltage is relatively high, the coil is shorted to ground to prevent absorption of RF power.

Charge control circuitry 206 controls the charging of battery 154. Charge control circuitry 206 uses the measurement functionality of battery measurement circuitry 208 to detect the state of battery 154. Battery measurement circuitry 208 may measure the battery voltage, charging current, battery discharge current, and/or the like. Using the battery voltage measurement of circuitry 208, charge control circuitry 206 may prevent battery charging when an end-of-life (EOL) state has been reached for battery 154. Also, charge control circuitry 206 may use a number of measurements to conduct fast charging operations as disclosed in greater detail in U.S. Patent Application Publication No. 2006/0259098, entitled "SYSTEMS AND METHODS FOR USE IN PULSE GENERATION." Charge control circuitry 206 also preferably monitors the output signal from bridge measure circuitry 204 to further regulate the output voltage from coil and bridge rectifier circuitry 203.

Figure 3:
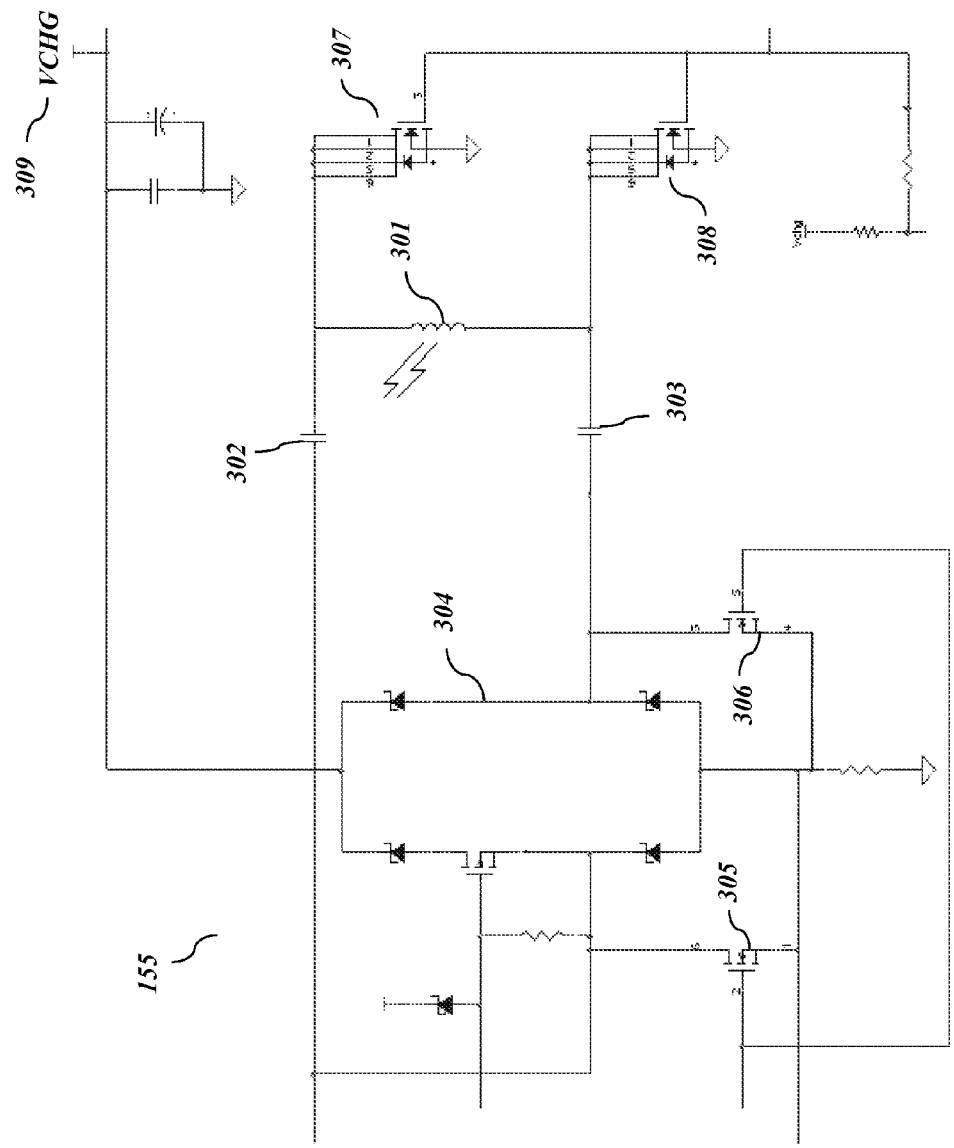
FIG. 3 depicts circuitry for controlling a charging coil within an implantable pulse generator according to one representative embodiment.

FIG. 3 depicts a portion of charging and communication circuitry 155 in more detail according to one representative embodiment. As shown in FIG. 3, circuitry 155 comprises coil 301 for inductively coupling with the coil of charger 100. Specifically, coil 301 and capacitors 302 and 303 are preferably tuned to capture RF power at one or more frequencies. In one preferred embodiment, coil 301 and capacitors 302 and 303 are tuned to receive power at a first RF frequency from external charger 100 and at a second RF frequency from a separate physician-patient programmer device (not shown).

The RF power is rectified by bridge rectifier 304. The output of rectifier 304 is shown in FIG. 3 as the node VCHG 309. The voltage on VCHG 309 is used to charge the battery assuming all necessary conditions are met. FETs 307 and 308 are used by primary regulatory circuitry 207 to regulate the voltage on VCHG 309 during charging operations. In one embodiment, primary regulatory circuitry 207 employs a band-gap comparison to regulate the voltage on VCHG 309. When the voltage is below the bottom threshold value (e.g., 4.77V) of the band-gap, regulatory circuitry 207 turns off FETs 307 and 308 and coil 301 absorbs RF power. When the voltage is above the top threshold value (e.g., 4.93V) of the band-gap, regulatory circuitry 207 turns on FETs 307 and 308 to short coil 301 to ground thereby preventing absorption of RF power.

Charge control circuitry 206 uses FETs 305 and 306 to respond to an error condition or to prevent an over-voltage condition on VCHG 309. In one embodiment, when the voltage on VCHG 309 is above approximately 6.5V, charge control circuitry 206 clamps the bridge inputs using FETs 305 and 306 to ground to stop energy absorption by coil 301 as a redundant safety mechanism.

During charging operations, status messages are communicated by charger transmitter 205 using FETs 305 and 306. The one-way communication occurs by controlling a 3 kHz modulation of coil 301 by charger transmitter 205. When communication of a status message is desired, charger transmitter 205 toggles its output to FETs 305 and 306 at 3 kHz with a data rate set at 300 baud. Error conditions and a charge-complete condition are examples of charging states that can be communicated using charger transmitter 205.

Figure 4:
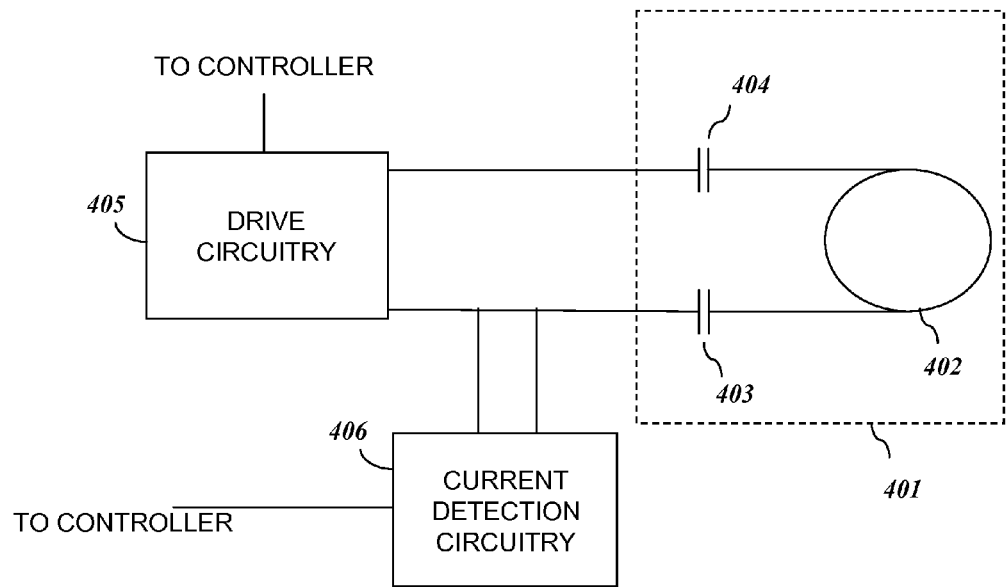
FIG. 4 depicts a charging wand coupled to selected circuitry of an external charger according to one representative embodiment.

FIG. 4 depicts charging wand 401 coupled to selected circuitry of external charger 100 according to one representative embodiment. Charging wand 401 comprises coil 402 and capacitors 403 and 404. Coil 402 and capacitors 403 and 404 are preferably tuned to radiate RF power efficiently at the frequency selected for charging IPG 150. Drive circuitry 405 generates an RF signal at the selected frequency to drive coil 402. Current detection circuitry 406 is used to detect the current flowing through coil 402. Current detection circuitry 406 can be implemented in any number of ways. For example, a current transformer may be employed to detect the current flowing through coil 402 according to one embodiment. Alternatively, a connection to ground through one or more high resistance resistors could be used to facilitate the current measurement.

Figure 5:
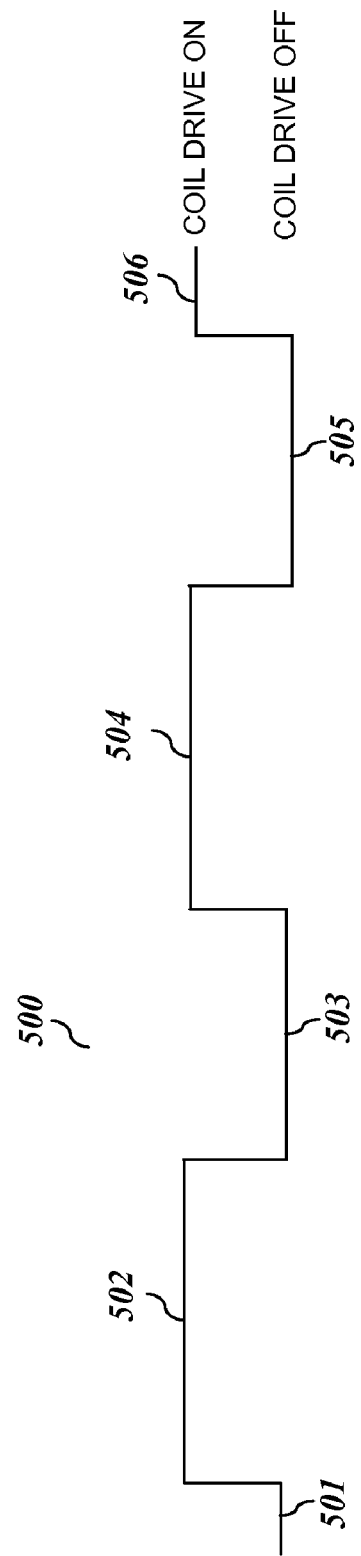
FIG. 5 depicts a duty cycle for driving a coil of an external charging device according to one representative embodiment.

In representative embodiments, drive circuitry 405, under the control of controller 151, drives coil 402 at the selected frequency according to a duty cycle. As shown in FIG. 5, drive signal 500 is preferably applied to drive circuitry 405. In FIG. 5, drive signal 500 is low at times 501, 503, and 505. When drive signal 500 is low, drive circuitry 405 does not generate the RF signal to drive coil 402. Drive signal 500 is high at times 502, 504, and 506. When drive signal 500 is high, drive circuitry 405 generates the RF signal to drive coil 402. The duty cycle defines the amount of time that drive signal 500 is high relative to the amount of time that drive signal 500 is low.

The duty cycle of drive signal 500 is preferably controlled by controller 151 to expend a minimal amount of power charging IPG 150. As previously noted, during charging operations, IPG 150 operates to clamp its coil 301 to ground when a charging voltage exceeds a certain limit. When coil 301 of IPG 150 is clamped to ground, the RF power radiated by external charger 100 is wasted, because no usable power is coupled into coil 301 of IPG 150. By modifying the duty cycle of the RF power signal radiated by external charger 100, the amount of time that coil 301 of IPG 150 is clamped to ground can be minimized, thereby minimizing the power wasted by external charger 100.

Figure 6:
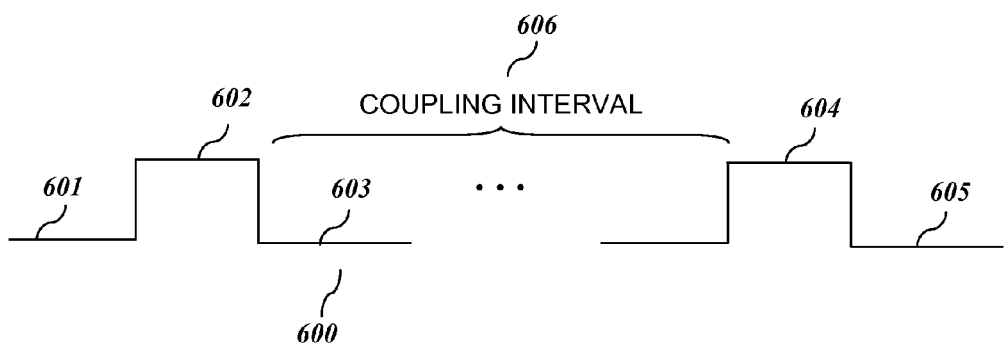
FIG. 6 depicts a signal indicative of current flowing through a coil of a charging wand according to one representative embodiment.

When charging wand 401 is placed within relatively close proximity of IPG 150, the current flowing through coil 402 depends upon whether coil 301 is clamped to ground or not. FIG. 6 depicts signal 600 generated by current detection circuitry 406 according to one representative embodiment. As shown in FIG. 6, time segments 601, 603, and 605 indicate an amount of current flowing through coil 402 while coil 301 of IPG 150 is absorbing power (i.e., is not clamped to ground). Time segments 602 and 604 indicate an amount of current flowing through coil 402 while coil 301 of IPG 150 is not absorbing power (i.e., is clamped to ground). Coupling interval 606 represents an amount of time between respective occasions when coil 301 is not absorbing power. The current flowing through coil 402 may increase or decrease when coil 301 is clamped to ground. The change in current will depend upon the tuning of coil 402 and capacitors 403 and 404 relative to the selected frequency for the RF power signal.

If coupling interval 606 is relatively short, external charger 100 is radiating excessive power on average. The power radiated by external charger 100 is repeatedly causing the voltage on VCHG 309 to exceed a defined amount. In that case, modifying the duty cycle of drive circuitry 405 permits charging to occur in a more efficient manner from the perspective of external charger 100. That is, the duty cycle can be modified to cause drive circuitry 405 to spend less time generating the RF power signal and, hence, to expend less energy in charging IPG 150.

Figure 7:
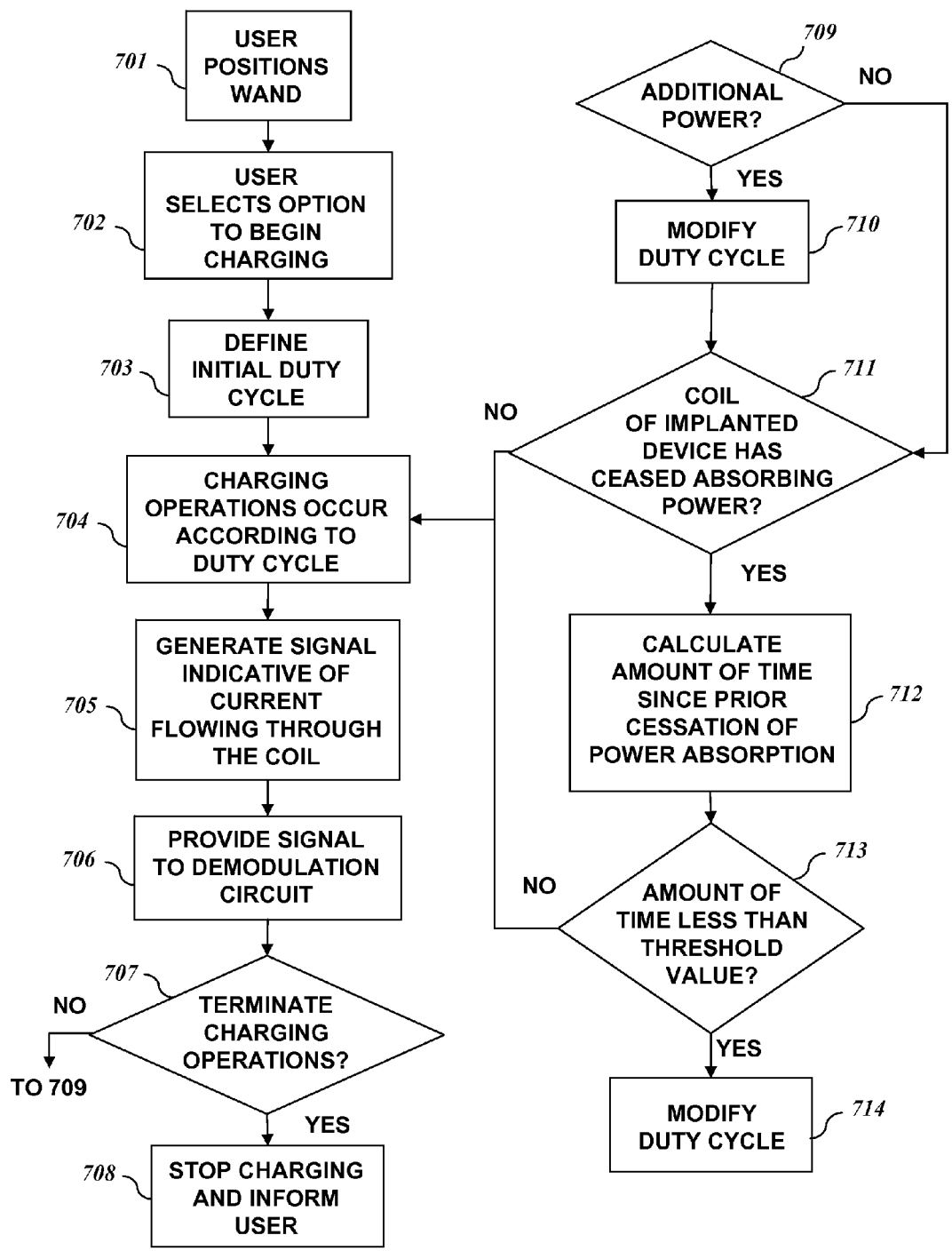
FIG. 7 depicts a flowchart for conducting charging operations according to one representative embodiment.

FIG. 7 depicts a flowchart for operating an external charging device for charging an implantable medical device according to one representative embodiment. In some embodiments, appropriate portions of the flowchart of FIG. 7 can be implemented using software instructions or code executing on a controller or processor of the external charging device to control the various hardware circuits of the external charging device.

In 701, a user positions a charging wand adjacent to the patient's body at a location near to the implant site of the implantable medical device to be recharged. In 702, the user selects an option on the external charging device to begin charging operations.

In 703, an initial duty cycle is selected or defined for charging operations. In 704, charging operations occur by driving the coil of the charging wand at a suitable RF frequency according to the selected duty cycle.

In 705, a signal indicative of the current flowing through the coil is generated. In 706, the signal is provided to a demodulation circuit to detect charging status messages communicated from the implanted medical device. Alternatively, the signal may be sampled and processed by a suitable signal processing routine to demodulate the charging status messages. The signal can be sampled using an on-chip analog-to-digital converter of the microcontroller of the external charging device.

In 707, a logical comparison is made to determine whether a status message indicates the charging operations should be terminated. If so, charging stops and a suitable message is provided to the user (708). The message may indicate to the user that the battery of the implantable medical device is fully charged, the battery has reached an end-of-life (EOL) state and should be replaced, or some error or malfunction has taken place. If the logical comparison indicates that charging should continue, the process flow continues to 709.

In 709, a logical comparison is made to determine whether additional power is appropriate. If so, the process flow proceeds to 710 where the duty cycle is modified to drive the coil a greater amount of time. From 710, the process flow returns to 704 to continue charging operations according to the newly selected duty cycle. If the logical comparison determines that additional power is not appropriate, the process flow proceeds from 709 to 711.

In 711, the signal indicative of current flow through the coil is processed to identify whether the coil of the implantable medical device has ceased absorbing RF power. If so, the process flow continues to 712. If not, the process flow returns to 704 to continue charging operations.

In 712, an amount of time is calculated since the preceding time that the coil of the implantable medical device ceased absorbing RF power. In 713, the calculated amount of time is compared to a threshold value. If the amount of time is greater than the threshold value, the process flow returns to 704 to continue charging operations. If the amount of time is less than the threshold value, the process flow proceeds to 714. In 714, another value is selected for the duty cycle to drive the coil less often. The process flow returns to 704 to continue charging operations according to the newly selected duty cycle. In an alternative embodiment, an averaging algorithm could be employed in which the total number of times that the coil of the implantable medical device ceased absorbing RF power within a time window is used to determine whether to modify the duty cycle.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

What is claimed:

1. A stimulation system, comprising:
   (i) an implantable pulse generator (IPG) that comprises:
   a first rechargeable battery for powering the IPG;
   pulse generating circuitry;
   a first coil for receiving RF power;
   a rectifier coupled to the coil; and
   first control circuitry for controlling RF power conversion, wherein the first control circuitry prevents the coil from absorbing RF power for conversion by the rectifier when a power conversion voltage exceeds a predefined level;
   and
   (ii) an external charging device for recharging the IPG, comprising:
   a second rechargeable battery for powering the external charging device;
   a second coil for radiating RF power;
   drive circuitry for driving the second coil according to a duty cycle;
   circuitry for generating a signal that is indicative of an amount of current flowing through the second coil; and
   second control circuitry for controlling the drive circuitry, wherein the second control circuitry is operable to process the signal from the circuitry for generating to detect when the first coil temporarily ceases absorbing RF power, the second control circuitry modifying the duty cycle in response to detection of the first coil temporarily ceasing absorbing RF power.

2. The system of claim 1 wherein the second control circuitry comprises a microcontroller for executing code that processes samples of the signal from the circuitry for generating.

3. The system of claim 1 wherein the second control circuitry is operable to measure an amount of time between successive occasions when the first coil temporarily ceases absorbing RF power.

4. The system of claim 1 wherein the second control circuitry is operable to count a number of times that the first coil temporarily ceases absorbing RF power within a defined amount of time.

5. The system of claim 1 wherein the second rechargeable battery is a rechargeable lithium ion battery.

6. The system of claim 1 wherein the second coil is disposed in a removable charging wand.

7. The system of claim 1 wherein the first control circuitry is operable to clamp the first coil to ground to cause the first coil to temporarily cease absorbing RF power.

8. A method of charging a medical device implanted with a human body using an external charging device, comprising:
   selecting a duty cycle on the external charging device;
   driving a first coil, by the external charging device, to radiate RF power according to the selected duty cycle;
   absorbing RF power by a second coil in the implanted medical device;
   converting the radiated RF power in the implanted medical device to electrical power;
   detecting, in the implanted medical device, that a RF conversion voltage has exceeded a defined limit;
   temporarily ceasing absorption of RF power by the second coil for conversion to electrical power in the implanted medical device;
   detecting, by the external charging device, when the second coil of the implantable medical device temporarily ceases absorbing RF power; and
   modifying the duty cycle for driving the first coil in response to the detecting when the coil of the implantable medical device temporarily ceases absorbing RF power.

9. The method of claim 8 wherein the detecting when the second coil of the implantable medical device temporarily ceases absorbing RF power further comprises:
   measuring an amount of time between successive occasions when the first coil temporarily ceases absorbing RF power.

10. The method of claim 8 wherein the detecting when the second coil of the implantable medical device temporarily ceases absorbing RF power further comprises:
    counting a number of times that the first coil temporarily ceases absorbing RF power within a defined amount of time.

11. The method of claim 8 wherein the external charging device is powered by a rechargeable lithium ion battery.

12. The method of claim 8 wherein the first coil is disposed in a removable charging wand.

13. The method of claim 8 wherein the temporarily ceasing absorption of RF power comprises:
    clamping the first coil to ground to cause the first coil to temporarily cease absorbing RF power.

14. The method of claim 8 wherein the duty cycle is selected by modified by a microcontroller of the external charging device.

* * * * *